(12) United States Patent
Li et al.

(10) Patent No.: US 10,980,733 B2
(45) Date of Patent: *Apr. 20, 2021

(54) COSMETIC COMPOSITIONS CONTAINING ACRYLIC THICKENER

(71) Applicant: L'ORÉAL, Paris (FR)

(72) Inventors: Chunhua Li, Hillsborough, NJ (US);
Hy Si Bui, Piscataway, NJ (US);
Dhaval Patel, Edison, NJ (US);
Mohamed Kanji, Edison, NJ (US);
Geoffrey White, Old Bridge, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,992

(22) Filed: Oct. 16, 2018

(65) Prior Publication Data

US 2019/0110976 A1     Apr. 18, 2019

Related U.S. Application Data

(63) Continuation of application No. 13/696,145, filed as application No. PCT/US2011/035361 on May 5, 2011, now Pat. No. 10,143,645.

(60) Provisional application No. 61/331,609, filed on May 5, 2010.

(51) Int. Cl.
*A61K 8/81* (2006.01)
*A61K 8/31* (2006.01)
*A61Q 1/10* (2006.01)
*A61K 8/58* (2006.01)

(52) U.S. Cl.
CPC .............. *A61K 8/8158* (2013.01); *A61K 8/31* (2013.01); *A61K 8/585* (2013.01); *A61K 8/8147* (2013.01); *A61K 8/8152* (2013.01); *A61Q 1/10* (2013.01); *A61K 2800/31* (2013.01)

(58) Field of Classification Search
CPC ..... A61K 2800/31; A61K 8/8147; A61Q 1/10
See application file for complete search history.

(56) References Cited

U.S. PATENT DOCUMENTS

| 6,986,895 | B2 * | 1/2006 | Suares | ................... A61K 8/365 424/401 |
| 7,837,984 | B2 | 11/2010 | McNamara | |
| 7,846,424 | B2 | 12/2010 | McNamara et al. | |
| 2003/0118619 | A1 | 6/2003 | Suares et al. | |
| 2005/0061348 | A1 * | 3/2005 | Patel | ................... A61K 8/731 132/218 |
| 2005/0175563 | A1 | 8/2005 | McNamara et al. | |
| 2006/0088486 | A1 | 4/2006 | McNamara et al. | |
| 2006/0093564 | A1 * | 5/2006 | Russ | ................... A61K 8/025 424/63 |
| 2006/0194932 | A1 | 8/2006 | Farcet | |
| 2006/0216257 | A1 | 9/2006 | Pays et al. | |
| 2009/0047309 | A1 | 2/2009 | Maes et al. | |
| 2009/0068132 | A1 | 3/2009 | Bratescu et al. | |
| 2009/0220481 | A1 | 9/2009 | Maes et al. | |
| 2010/0028317 | A1 | 2/2010 | Maes et al. | |
| 2010/0080845 | A1 | 4/2010 | Maes et al. | |
| 2010/0215755 | A1 | 8/2010 | Bratescu et al. | |
| 2011/0274636 | A1 | 11/2011 | Perruna et al. | |
| 2012/0171141 | A1 | 7/2012 | Bui et al. | |
| 2012/0171142 | A1 | 7/2012 | Bui et al. | |
| 2012/0171145 | A1 | 7/2012 | Bui et al. | |
| 2012/0315076 | A1 | 12/2012 | Bekele | |
| 2014/0193351 | A1 | 7/2014 | Mohammadi | |

FOREIGN PATENT DOCUMENTS

| EP | 0 388 582 | 9/1990 |
| EP | 0 749 746 | 12/1996 |
| EP | 1 604 632 | 12/2005 |
| EP | 1 674 076 | 6/2006 |
| JP | 2005-330203 | 2/2005 |
| KR | 2007/0094367 | 9/2007 |
| WO | WO 0245662 | 6/2002 |
| WO | WO-0245662 A2 * | 6/2002 ............... A61K 8/38 |

OTHER PUBLICATIONS

CARBOPOL 934 Polymer Product Specifications (Published Jun. 26, 2008; accessed May 8, 2013) (Year: 2008).*
ViscUp Ez (www.archpersonalcare.com). Technical information. Published Feb. 21, 2007 (Year: 2007).*
Bernard, P.; Merat, E.; Braun, O.; Mallo, P. "A New Polymer with a MAXimum Resistance to Electrolytes" SOFW—Journal, Dec. 2010, 136, 55-58. (Year: 2010).*
Supplementary European Search Report as received in the corresponding EP Patent Application No. 11778347.2-1458/2566441 dated Dec. 2, 2015.
Database WPI, Week 200603, Thomson Scientific, London, GB; AN 2006-022972, XP002750775.
Database GNPD Mintel: Jan. 2010, Fidelity Long lash mascara, XP002750776, Database accession No. 1253106, *Abstract*.
Bernard, P., et al., "A New Polymer with a MAXimum Resistance to Electrolytes" SOFW—Journal, Dec. 2010, 136, pp. 55-58.
Office Action dated May 29, 2017, in Brazilian Patent Application No. BR112012028274-3.
European Office Action dated May 16, 2017, in Patent Application No. 11 778 347.2.
Office Action as received in the corresponding Chinese Patent Application No. 201180033311.2 dated Jun. 30, 2014 w/English Translation.
CARBOPOL 934 Polymer Product Specifications (Published Jun. 26, 2008; accessed May 8, 2013).

(Continued)

*Primary Examiner* — Andrew S Rosenthal
(74) *Attorney, Agent, or Firm* — Oblon, McClelland, Maier & Neustadt, L.L.P.

(57) ABSTRACT

The invention relates to a composition, especially a cosmetic composition, comprising at least one acrylic thickener and at least one oil, as well as to methods of using such compositions.

18 Claims, No Drawings

(56) References Cited

OTHER PUBLICATIONS

Ethanol MSDS (sigma-aldrich.com), accessed May 31, 2013.
Dipropylene glycol MSDS (sigma-aldrich.com), accessed May 31, 2013.
ViscUp Ez (www.archpersonalcare.com). Technical Information. Published Feb. 21, 2007.
Combined Office Action and Search Report dated Oct. 24, 2013 in Chinese Application No. 201180033311.2.
Glycerin MSDS (sigma-aldrich.com), accessed May 31, 2013.
International Search Report dated Feb. 8, 2012 in PCT/US11/35361 Filed May 5, 2011.

* cited by examiner

COSMETIC COMPOSITIONS CONTAINING ACRYLIC THICKENER

CROSS-REFERENCE TO RELATED APPLICATIONS

This application is a Continuation Application of U.S. Ser. No. 13/696,145, filed Jan. 11, 2013, which is a National Stage of PCT/US2011/035361, filed May 5, 2011, which claims the benefit of priority under 35 U.S.C. § 119(e) from U.S. Provisional Application Ser. No. 61/331,609, filed May 5, 2010, the entire contents of which is hereby incorporated by reference.

FIELD OF THE INVENTION

The present invention relates to compositions comprising at least one acrylic thickener. Among other improved or beneficial properties, compositions containing an acrylic thickener have surprisingly good removal properties.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to posses good feel and texture upon application. Unfortunately, many of these compositions can be difficult to apply and do not possess a soft texture or smooth feel upon application. Moreover, such compositions oftentimes have a tendency to feel tacky, yielding poor application and spreadability characteristics, and can be difficult to remove.

Silicone elastomers have been added to cosmetic compositions to improve the feel of the compositions. However, the use of silicone elastomers can be problematic, given their expense and that they can be difficult to formulate owing to their chemical make up—for example, compositions including silicone elastomers can be unstable, particularly if uncomplimentary compounds are added to an elastomer-containing composition.

Thus, there remains a need for improved cosmetic compositions having improved cosmetic properties, particularly good feel and texture characteristics upon application, without relying solely (if at all) upon silicone elastomers, and which can be easily removed.

Accordingly, one aspect of the present invention is a care and/or makeup and/or treatment composition for keratinous material which has good cosmetic properties such as, for example, good feel and/or texture properties upon application, and/or good removability.

SUMMARY OF THE INVENTION

The present invention relates to compositions comprising at least one acrylic thickener. Preferably, the compositions are anhydrous.

The present invention also relates to colored compositions comprising at least one coloring agent and at least one acrylic thickener. Such colored compositions can be, for example, cosmetic compositions such as lip compositions (for example, lipstick or liquid lip colors), mascaras, eyeshadows or foundations. Preferably, the compositions are anhydrous.

The present invention also relates to methods of treating, caring for and/or making up keratinous material (for example, skin, eyes, eyelashes or lips) by applying compositions of the present invention comprising at least one acrylic thickener, preferably anhydrous compositions, to the keratinous material in an amount sufficient to treat, care for and/or make up the keratinous material.

The present invention also relates to methods of enhancing the appearance of keratinous material (for example, skin, eyes, eyelashes, or lips) by applying compositions of the present invention comprising at least one acrylic thickener, preferably anhydrous compositions, to the keratinous material in an amount sufficient to enhance the appearance of the keratinous material.

The present invention also relates to methods of volumizing eyelashes comprising applying a mascara composition of the present invention comprising at least one acrylic thickener, preferably an anhydrous mascara composition.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention comprising the at least one acrylic thickener contain no water.

The compositions discusses below may be in any form, either liquid or non-liquid (semi-solid, soft solid, solid, etc.). For example, they may be a paste, a solid, a gel, or a cream. They may be an emulsion, such as an oil-in-water or water-in-oil emulsion, a multiple emulsion, such as an oil-in-water-in-oil emulsion or a water-in-oil-in-water emulsion, or a solid, rigid or supple gel. The compositions of the invention may, for example, comprise an external or continuous fatty phase. The compositions can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Acrylic Thickener

According to the present invention, compositions comprising at least one acrylic thickener are provided. "Acrylic thickener" as used herein refers to polymers based upon one or more (meth)acrylic acid (and corresponding (meth)acrylate) monomers or similar monomers.

According to preferred embodiments, the acrylic thickener is an anionic acrylic polymer comprising at least one monomer performing a weak acid function such as, for example, acrylic acid, methacrylic acid, itaconic acid, crotonic acid, maleic acid and/or fumaric acid.

According to preferred embodiments, the acrylic thickener is an anionic acrylic polymer further comprising at least one monomer performing a strong acid function such as, for example, monomers having a function of the sulfonic acid type or phosphonic acid type, such as 2-acrylamido-2-methylpropane sulfonic acid (AMPS).

According to preferred embodiments, the anionic acrylic polymer may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxydes.

Particularly preferred acrylic thickeners are disclosed in U.S. patent application publication nos. 2004/0028637 and 2008/0196174, the entire contents of both of which are incorporated herein by reference. Particularly preferred acrylic thickeners are sodium acrylate/sodium acryloyldimethyl taurate copolymers.

A particularly preferred commercially available product containing an acrylic thickener is that sold under the INCI name Sodium Acrylate/Sodium Acryloyldimethyl Taurate Copolymer & Hydrogenated Polydecene & Sorbitan Laurate & Trideceth-6 which is marketed by Arch Personal Care Products, South Plainfield, N.J., USA under the tradename ViscUp® EZ. Other commercially available products include SEPPIC's Sepiplus S (hydroxyethyl acrylate sodium acryloyldimethyl taurate copolymer and polyisobutene and PEG-7 trimethyloylpropane coconut ether) and Sepinov EMT 10 (hydroxyethyl acrylate sodium acryloyldimethyl taurate copolymer).

According to preferred embodiments of the present invention, the acrylic thickener is in powder form. Suitable examples of such a thickener include Sepinov EMT 10 discussed above and Sepimax Zen (polyacrylate crosspolymer 6).

According to preferred embodiments of the present invention, the acrylic thickener comprises an acrylamide monomer. For example, SEPPIC's Simulgel 600 (acrylamide/sodium acryloyldimethyltaurate copolymer/isohexadecane/polysorbate 80) is an acceptable thickener.

Preferably, the acrylic thickener(s) represent from about 0.1% to about 20% of the total weight of the composition, more preferably from about 1% to about 10% of the total weight of the composition, and most preferably from about 2.5% to about 7.5% of the total weight of the composition, including all ranges and subranges therebetween.

Oil

According to the present invention, compositions comprising at least one oil are provided. "Oil" means any non-aqueous medium which is liquid at ambient temperature (25° C.) and atmospheric pressure (760 mm Hg).

Suitable oils include volatile and/or non-volatile oils. Such oils can be any acceptable oil including but not limited to silicone oils and/or hydrocarbon oils.

According to certain embodiments, the composition of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the composition of the present invention preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments of the present invention, the oil is a high viscosity oil which is a silicone oil and/or a hydrocarbon oil. "High viscosity" means an oil having a viscosity greater than 250 cSt at 25° C.

Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenyldimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

Suitable examples of such hydrocarbon oils include, but are not limited to, fluids having a molecular mass of more than 500 g/mol, for example more than 600 g/mol, and for example more than 650 g/mol. By "hydrocarbon" compound, it is meant a compound comprising principally atoms of carbon and hydrogen and optionally one or more functional groups chosen from hydroxyl, ester, ether and carboxyl functions. These compounds are, according to one aspect, devoid of —Si—O— groups. Suitable examples of hydrocarbon fluids include, but are not limited to polybutylenes, such as Indopol H-100 (of molar mass or MM=965 g/mol), Indopol H-300 (MM=1 340 g/mol), and Indopol H-1500 (MM=2 160 g/mol), which are sold or manufactured by Amoco; hydrogenated polyisobutylenes, such as Panalane H-300 E, sold or manufactured by Amoco (M=1 340 g/mol), Viseal 20000 sold or manufactured by Synteal (MM=6 000 g/mol), and Rewopal PIB 1000, sold or manufactured by Witco (MM=1 000 g/mol); polydecenes and hydrogenated polydecenes, such as Puresyn 10 (MM=723 g/mol) and Puresyn 150 (MM=9 200 g/mol) sold or manufactured by Mobil Chemicals; esters such as linear fatty acid esters having a total carbon number ranging from 30 to 70, such as pentaerythrityl tetrapelargonate (MM=697.05 g/mol); hydroxy esters, such as diisostearyl malate (MM=639 g/mol); aromatic esters such as tridecyl trimellitate (MM=757.19 g/mol); esters of C24-C28 branched fatty acids or fatty alcohols, such as those described in EP-A-0 955 039, for example triisocetyl citrate (MM=856 g/mol), pentaerythrityl tetraisononanoate (MM=697.05 g/mol), glyceryl triisostearate (MM=891.51 g/mol), glyceryl 2-tridecyltetradecanoate (MM=1 143.98 g/mol), pentaerythrityl tetraisostearate (MM=1 202.02 g/mol), poly-2-glyceryl tetraisostearate (MM=1 232.04 g/mol) and pentaerythrityl 2-tetradecyltetradecanoate (MM=1 538.66 g/mol); and mixtures thereof. Suitable ester oils can also be described according to formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, with $R_1+R_2 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters. A particularly preferred ester is diisostearyl malate.

According to preferred embodiments, the at least one oil is present in the compositions of the present invention in an amount ranging from about 10 to about 65% by weight, more preferably from about 20 to about 50% by weight, and most preferably from about 30 to about 40% by weight, based on the total weight of the composition, including all ranges and subranges within these ranges.

According to preferred embodiments, the acrylic thickener and the oil(s) are present in the compositions of the present invention in a weight ratio of 1:2 to 1:20, preferably 1:3 to 1:15, and preferably 1:4 to 1:12, including all ranges and subranges therebetween.

Coloring Agents

According to preferred embodiments of the present invention, compositions further comprising at least one coloring agent are provided. Preferably, such colored compositions can be cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments, the compositions of the present invention contain less than 10% wax, preferably less than 5% wax, preferably less than 3% wax, preferably less than 2% wax, and preferably less than 1% wax.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention comprising at least one acrylic thickener are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to other embodiments of the present invention, methods of volumizing eyelashes are provided. These methods comprise applying a mascara composition of the present invention comprising at least one acrylic thickener to eyelashes.

According to other embodiments of the present invention, compositions having improved cosmetic properties such as, for example, increased removal properties are provided. Such compositions comprise at least one acrylic thickener. The improved removal properties result from the presence of the acrylic thickener. Exposure to substantial amounts of water causes the acrylic thickener to breakdown and the applied composition to breakdown, resulting in easier removal of the applied composition as discussed below.

According to preferred embodiments of the present invention, the compositions of the present invention can be removed using water or a composition comprising water. For example, the composition comprising water can be a "topcoat" containing water which, when applied to the mascara compositions of the present invention, facilitates removal of the mascara from the eyelashes. The amount of water to which the applied composition is exposed is sufficient to cause the acrylic thickener to breakdown to facilitate removal of the applied composition. Generally speaking, the amount of water applied to facilitate removal is preferably between 5 and 20 grams of water, preferably between 6 and 15 grams of water, and preferably between 7 and 10 grams of water.

According to preferred embodiments, the composition of the present invention and the water-containing composition (for example, topcoat) are present in a kit.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Comparative Mascaras

Procedure (1) Combined A1, A2 and A3, heated to 90-95° C. Homogenized for 30 mins until pigments were dispersed
(2) Added B1, mixed until dissolved, about 15 mins. Then Added B2 and B3, mix for 10 mins.
(3) Added C, Mixed for 10 mins.
(4) Added D, Mixed for 10 Mins.
(5) Switched to Paddle Mixing, Added E and F at 30-35° C.
(6) Dropped Batch at 25° C.

Experiment Results

Effect of Water-Sensitive Material on Removability

Mascaras were applied on fake lashes and dried for 1 hour. Then the fake lashes were immersed into water for 15 minutes. For 0% water sensitive material formula (control), mascara remained on the fake lashes and the water was clear. Similar results were found for the composition containing 5% Polysorbate 80. For the formula containing 7.5% Simulgel, mascara was partially removed into the water. For the formula representative of the invention having 5% Viscup-EZ, an even better removability was found: a higher % of mascara swelled into water and formed tube shape.

Demonstration of Tube Removal

Mascara was applied on fake lashes and dried for 1 hour. Then the fake lashes were immersed into water for 15 minutes. Subsequently the mascara was removed by a cotton pad and tubes were observed on the pad.

| Phase | Chemical Name | Control 1 % | Control 2 % | Inventive % |
|---|---|---|---|---|
| A1 | ETHYLENEDIAMINE/STEARYL DIMER DILINOLEATE COPOLYMER | 1 | 1 | 1 |
| A1 | Carnauba Wax | 4.7 | 4.7 | 4.7 |
| A1 | Bees Wax | 8.3 | 8.3 | 8.3 |
| A1 | ALLYL STEARATE/VA COPOLYMER | 3.3 | 3.3 | 3.3 |
| A1 | Polyvinyl Laurate | 2.2 | 2.2 | 2.2 |
| A1 | Hydrogenated Jojoba Oil | 0.1 | 0.1 | 0.1 |
| A1 | Rice Bran Wax | 2.8 | 2.8 | 2.8 |
| A1 | VP/EICOSENE COPOLYMER | 2 | 2 | 2 |
| A1 | Paraffin | 2.8 | 2.8 | 2.8 |
| A1 | Propyl Paraben | 0.19 | 0.19 | 0.19 |
| A1 | Methyl Paraben | 0.15 | 0.15 | 0.15 |
| A2 | Talc | 1 | 1 | 1 |
| A2 | Black Iron Oxide | 4.2 | 4.2 | 4.2 |
| A3 | Isododecane | 42.56 | 35.06 | 37.56 |
| B1 | Bentone | 5.8 | 5.8 | 5.8 |
| B2 | Polysorbate 20 | 2.66 | 2.66 | 2.66 |
| B3 | Polysorbate 80 | 5.34 | 5.34 | 5.34 |
| C | Propylene Carbonate | 1.9 | 1.9 | 1.9 |
| D | SODIUM ACRYLATE/SODIUM ACRYLOYLDIMETHYL TAURATE COPOLYMER (and) SORBITAN LAURATE (and) TRIDECETH-6 (Viscup) | 0 | 0 | 5 |
| D | ACRYLAMIDE/SODIUM ACRYLOYLDIMETHYLTAURATE COPOLYMER (and) ISOHEXADECANE (and) POLYSORBATE 80 (Simulgel) | 0 | 7.5 | 0 |
| E | *COPERNICIA CERIFERA* (CARNAUBA) WAX (and) PEG-30 GLYCERYL STEARATE | 7 | 7 | 7 |
| F | Denatured Alcohol | 2 | 2 | 2 |
| Total | | 100 | 100 | 100 |

Examples 2-4—Mascaras

Example 2

Example 2 Base Composition

| Chemical Name | Phase | Percent |
|---|---|---|
| Isododecane | A | 35.3 |
| Bentonite | A | 5.5 |
| Benzoic Acid | A | 0.1 |
| Black Iron Oxide | A | 6 |
| Talc | A | 1 |
| Carnauba Wax | A | 4.9 |
| Paraffin | A | 7.9 |
| Microcrystalline Wax | A | 8 |
| Viscup-EZ | A | 5 |
| Polysorbate-20 | A | 1 |
| Propylene Carbonate | B | 1.8 |
| | | 76.5 |

Example 2 Mascara Compositions

| Chemical Name | Phase | Percent |
|---|---|---|
| Isododecane | A | 23.5 |
| Base | B | 76.5 |
| | | 100 |
| Isododecane | A | 22.32 |
| MQ Resin | A | 1 |
| KP 561 P | A | 0.18 |
| Base | B | 76.5 |
| | | 100 |
| Isododecane | A | 20.56 |
| MQ Resin | A | 2.5 |
| KP 561 P | A | 0.44 |
| Base | B | 76.5 |
| | | 100 |
| Isododecane | A | 17.62 |
| MQ ResinBase | A | 5 |
| KP 561 P | A | 0.88 |
| Base | B | 76.5 |
| | | 100 |
| Isododecane | A | 0 |
| MQ Resin | A | 20 |
| KP 561 P | A | 3.5 |
| Base | B | 76.5 |
| | | 100 |

Example 3

| Chemical Name | Phase | Percent |
|---|---|---|
| Isododecane | A | 46.96 |
| Bentonite | A | 6.5 |
| Benzoic Acid | A | 0.1 |
| Black Iron Oxide | A | 6 |
| Talc | A | 3.5 |
| Uniclear | A | 1 |
| Carnauba Wax | A | 4.9 |
| Paraffin | A | 7.9 |
| Microcrystalline Wax | A | 8 |
| Kobo Guard | A | 4 |
| Viscup-EZ | A | 5 |
| Polysorbate-20 | A | 1 |
| Propylene Carbonate | B | 2.14 |
| Mexoryl SAP | C | 3 |
| | | 100 |

Example 3 Procedure:

1) Combine all of A, heat to 95° C. and homogenize for 1 hour.

2) Add B and homogenize for 10 minutes. Switch to paddle mixing.

3) Add C at 40° C., mix until batch reaches 25° C.

Example 4

Example 4 Base Composition

| Chemical Name | Phase | Percent |
|---|---|---|
| Isododecane | A | 46.96 |
| Bentonite | A | 6.5 |
| Benzoic Acid | A | 0.1 |
| Black Iron Oxide | A | 6 |
| Talc | A | 3.5 |
| Kobo Guard | B | 4 |
| Polysorbate-20 | B | 1 |
| Propylene Carbonate | B | 2.14 |
| Uniclear | C | 1 |
| Carnauba Wax | C | 4.9 |
| Paraffin | C | 7.9 |
| Microcrystalline Wax | C | 8 |
| Mexoryl SAP | D | 3 |
| | | 95 |

Example 4 Mascara Compositions

| Chemical Name | Phase | Percent |
|---|---|---|
| Simulgel 600 | A | 5 |
| Isododecane | A | 0 |
| Base | B | 95 |
| | | 100 |
| Sepiplus S | A | 5 |
| Isododecane | A | 0 |
| Base | B | 95 |
| | | 100 |
| Sepinov emt10 | A | 5 |
| Isododecane | A | 0 |
| Base | B | 95 |
| | | 100 |
| Sepimax Zen | A | 1.5 |
| Isododecane | A | 3.5 |
| Base | B | 95 |
| | | 100 |

Example 5—Application of Mascara to Eyelashes

The following mascara was prepared

| Chemical Name | Phase | Concentration |
|---|---|---|
| Isododecane | A | 46.96 |
| Distearyl Dimethyl Ammonium Hectorite | A | 6.5 |
| Colorant | A | 6 |
| Talc | A | 3.5 |
| Anox 20 | A | 1 |
| Carnauba Wax | A | 4.9 |
| Paraffin (refined, protected) | A | 7.9 |
| Microcrystalline Wax | A | 8 |
| Hydrogenated Polycyclopentadiene and isododecane | A | 4 |
| Sodium acrylate/sodium acryloydimethyl taurate copolymer & hydrogenated polydecene & sorbitan laurate & trideceth-6 | A | 5 |
| Oxyethylene (20) sorbitan monolaurate | A | 1 |
| Propylene carbonate | B | 2.14 |
| Carnauba wax microdispersion | C | 3 |

The formulation was applied and studied as discussed below.

Test 1

Objective:

To evaluate women perception on immediate cosmetic aspects, application, make up results, wear and comfort Methodology:

Semi qualitative interviews, monadic test

Parameters: Perception, application, make-up results, wear and comfort

Evaluation time: Upon application and 3 days home usage

Target:

10 women between 20 to 40 years.

Mascara usage frequency—At least once per week.

5 regular users of waterproof and 5 users of non water proof black mascara

Users of mix brands

Conclusion

| IMPORTANCE | ATTRIBUTES | |
|---|---|---|
| | PRINCIPAL QUALITIES OF THE INVENTION MASCARA | OTHER OBSERVATIONS |
| VERY IMPORTANT | Lashes well separated Visible lengthening effect Long wear - around 7 to 8 hours without any smudge particles and need to retouch | None |
| SOMEWHAT IMPORTANT | Easy and even spreading Narrow brush bristles that gives an even distribution with good volume Light and comfortable feel through the day. Easy removal - with water/ face wash/cleansing milk. | No outstanding volume effect, need to apply several strokes for desired result. Not easy removal - irritation and loss of few eye-lashes while removal. |

Test 2

Objective:

To evaluate women's perceptions on immediate cosmetic aspects, application, make up results, wear and comfort.

Methodology:

Semi qualitative interviews, Monadic test

Parameters: Perception, application, make-up results, wear and comfort

Evaluation time: Upon application and 3 days home usage

Target:

10 women aged 20-35

Regular users of waterproof, black mascara with at least 4 times/week. Users of mass brands only. Mascara with comb brush or double-end is excluded Conclusion

| IMPORTANCE | ATTRIBUTES | |
|---|---|---|
| | PRINCIPAL QUALITIES | OTHER OBSERVATIONS |
| VERY IMPORTANT | Lashes well separated Long wear around 10-13 hours i.e. no particle, no smudge, no need for retouching during the day Easy removal with water i.e. mascara come off melting as ink, no need to pull lashes Visible lengthening effect Dry quickly i.e. no messiness/ smudge on eyelids or under eyes | None |
| SOMEWHAT IMPORTANT | Easy spreading i.e. smooth, even spreading from roots to tips, no clump of mascara on lashes Curved brush - fit eye shapes making it easy to apply Narrow-teeth bristles - help separate lashes and able to access to each lash | Not outstanding volume effect, need to apply several strokes for desired result. Too short bristles - perceived to be a cause of less outstanding volume effect. |

Test 3

Parameters: Application, sensation, makeup result and daytime wearing

Experimental methods: One week home-use

Application Panel: In the women's usual makeup routine 10 women of 20-45 years old who use brush-type black waterproof mascara more than 5 days a week, and expect 'lengthening' effect from mascara Evaluation time: After one week home-use Major Characteristics

| Level of importance | POSITIVE (+) | NEGATIVE (−) |
|---|---|---|
| Very strong | Easy to remove | Brush applicator made application difficult |
| Somewhat strong | Did not smudge under the eyes during the day Lengthened the lashes, along with thickening the lashes moderately Spread smoothly | Gave an uneven distribution to the lashes Did not provide lash separation Flaked off during the day |

Test 4

Method and Protocol

Method: Semi-qualitative interviews

Parameters: Application, perceptions, make-up result, wear and comfort

Experimental method: Monadic test

Panel: 10 women (20-40 year old) who use mass brand black washable mascara at least 5 times weekly Evaluation time: Upon application and 3 days home usage Conclusion

| | ATTRIBUTES | |
|---|---|---|
| IMPORTANCE | PRINCIPAL QUALITIES | OTHER OBSERVATIONS |
| VERY IMPORTANT | Long wear of make-up results for 8-10 hours<br>Smudge-proof<br>Good separation lash by lash without clumps, lashes do not stick together<br>Easy to remove with warm water/usual cleanser/remover<br>Darkening effect | Poor lengthening effect<br>Not volume enough |
| SOMEWHAT IMPORTANT | A little curling effect | Easy to smudge eyelids when blinking eyes due to slow dryness and too wet texture |

What is claimed is:

1. A mascara comprising:
   polyacrylate crosspolymer 6;
   at least one wax;
   at least one coloring agent; and
   20 to 50% by weight of at least one non-silicone volatile oil selected from the group consisting of volatile hydrocarbon oils having 8 to 16 carbon atoms, volatile esters, volatile ethers, and mixtures thereof,
   wherein the mascara is removable from eyelashes using a second composition consisting essentially of water.

2. The mascara of claim 1, wherein the polyacrylate crosspolymer 6 and the non-silicone volatile oil(s) are present in a weight ratio of from 1:2 to 1:20.

3. The mascara of claim 1, wherein the polyacrylate crosspolymer 6 is in powder form.

4. The mascara of claim 1, wherein the polyacrylate crosspolymer 6 is present in an amount of 0.1% to 20% by weight of the weight of the mascara.

5. A method of making up eyelashes comprising applying the mascara of claim 1 to the eyelashes.

6. A method of volumizing eyelashes comprising applying the mascara of claim 1 to the eyelashes.

7. A method of removing the mascara according to claim 1 from eyelashes comprising applying water to the mascara in an amount sufficient to remove the mascara from the eyelashes.

8. The mascara according to claim 1, wherein the mascara further comprises at least one volatile silicone oil selected from the group consisting of octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and mixtures thereof.

9. The mascara according to claim 1, wherein the non-silicone volatile oil is one or more hydrocarbon oil having from 8 to 16 carbon atoms.

10. The mascara according to claim 1, wherein the non-silicone volatile oil is selected from the group consisting of propylene glycol n-butyl ether, ethyl 3-ethoxypropionate, propylene glycol methylether acetate, and mixtures thereof.

11. The mascara according to claim 1, wherein the at least one non-silicone volatile oil is present in an amount of from 30 to 40% by weight, based on the total weight of the mascara.

12. The mascara according to claim 1, wherein the non-silicone volatile oil is selected from the group consisting of isoparaffin, isododecane, and mixtures thereof.

13. The mascara according to claim 1, wherein the polyacrylate crosspolymer 6 and the non-silicone volatile oil(s) are present in a weight ratio of from 1:3 to 1:15.

14. The mascara according to claim 1, wherein the polyacrylate crosspolymer 6 and the non-silicone volatile oil(s) are present in a weight ratio of from 1:4 to 1:12.

15. The mascara according to claim 1, wherein the coloring agent is at least one pigment.

16. The mascara according to claim 15, wherein the pigment is iron oxide.

17. The mascara according to claim 15, wherein the pigment is present in an amount of from 0.5% to 40% by weight, based on the total weight of the mascara.

18. The mascara according to claim 1, wherein the mascara is capable of providing a visible lengthening effect to eyelashes.

* * * * *